United States Patent [19]

Papadopoulos

[11] Patent Number: 5,627,216

[45] Date of Patent: May 6, 1997

[54] MEDICINAL OINTMENT FOR HEMORRHOID AND SKIN CARE

[76] Inventor: George D. Papadopoulos, P.O. Box 11686, Costa Mesa, Calif. 92627

[21] Appl. No.: 418,278

[22] Filed: Apr. 7, 1995

Related U.S. Application Data

[63] Continuation-in-part of Ser. No. 192,630, Feb. 7, 1994, abandoned.

[51] Int. Cl.⁶ .................................................. A61K 35/78
[52] U.S. Cl. ...................... 514/783; 424/195.1; 514/882; 514/886; 514/887
[58] Field of Search ...................... 514/783, 859, 514/860, 861, 862, 863, 864, 865, 882, 887; 424/195.1

[56] References Cited

U.S. PATENT DOCUMENTS

| 4,514,384 | 4/1985 | Gallina | 514/179 |
| 5,194,654 | 3/1993 | Hostetler et al. | 558/152 |
| 5,229,130 | 7/1993 | Sharma et al. | 424/449 |
| 5,460,821 | 10/1995 | Masiz | 424/449 |

*Primary Examiner*—John Kight
*Assistant Examiner*—Howard C. Lee
*Attorney, Agent, or Firm*—Lewis C. Massie

[57] ABSTRACT

A composition made from eggplant for the treatment of hemorrhoids is disclosed. A composition which effectively reduces swelling and pain in the anal area is formed by mixing powdered eggplant leaves and boiling virgin olive oil in a covered container for approximately 30 minutes.

1 Claim, No Drawings

MEDICINAL OINTMENT FOR HEMORRHOID AND SKIN CARE

This application is a continuation in part of application Ser. No. 08/192,630, filed Feb. 7, 1994, now abandoned.

BACKGROUND OF THE INVENTION

1. Field of the Invention

The instant invention relates to the field of medicinal compounds and, in particular my invention is concerned with a medicinal compound formed by boiling eggplant stalk and stem in virgin olive oil.

2. Description of the Related Art

Medical compounds formed from an aqueous solution of various plant leaves and water have long been known. A pertinent prior art patent U.S. Pat. No. 4,261,981, Apr. 14, 1981, issued to Sam Humphrey. This patent refers to a combination made from ragweed for the treatment of diarrhea, intestinal disorders, ulcers and hemorrhoids. The patent describes a composition formed by mixing ragweed leaves and water and boiling the resulting mixture in a covered container for 20 to 30 minutes.

SUMMARY OF THE INVENTION

The instant invention describes the composition wherein eggplant, a genus of Solanum melongena the soft green skin of the stalk or stem which is dried by exposure to the sun or low heat oven then ground to the consistency of a fine powder. The powder is then mixed with virgin olive oil and exposed to heat until the virgin olive oil mixture is at a boiling temperature at which time the powder is added to the receptacle with the boiling virgin olive oil for approximately 30 minutes.

DETAILED DESCRIPTION OF THE PREFERRED EMBODIMENTS

The soft green skin of the stalk and stem of the eggplant, which is carefully separated from the hard supporting structure, is subsequently dried by exposure to the sun or a low heat oven, then ground to the consistency of a very fine powder.

Mix an ointment of a ratio of 5 grams of ground fine powder to one quart of boiling virgin olive oil. Said powder is then placed into a receptacle containing virgin olive oil which is then exposed to a heat source until the virgin olive oil achieves a boiling temperature at which time the fine powder is added to the receptacle with the boiling virgin olive oil. The temperature of the virgin olive oil continues to rise after the powder is added. The mixture is allowed to boil for approximately 30 minutes after which the manufacturing process is completed.

Instructions for using the ointment:

Before applying the liquid ointment, thoroughly clean the affected area. The liquid ointment should be applied topically either manually or by a swab. Apply the liquid ointment twice daily, once on awakening in the morning and once in the evening at retirement. Mid-day application of the liquid ointment is optional.

This mixture has proven successful in reducing the irritation of hemorrhoids and improving skin texture by reducing sun parched wrinkles.

The following examples show the effectiveness of the Solanum melongena-virgin olive oil composition.

EXAMPLE 1

A 43 year old male suffering from hemorrhoids applied the Solanum melongena-virgin olive oil composition to the affected area 2 times daily for 2 months. Relief from pain occurred after two weeks and the hemorrhoids completely disappeared after 6 weeks. No side effects were observed. Subsequent applications for treatment of hemorrhoids yielded similar results with no side effects.

EXAMPLE 2

A 36 year old male suffering from hemorrhoids over a 20 year span, applied the Solanum melongena-virgin olive oil composition to the affected area twice a day for 2 years. A longer time was necessary for curing his hemorrhoid condition because the treatment was intermittently applied and halted during the 2 year period. He is now totally cured of hemorrhoids from applying this composition. As a safety measure, he applies the Solanum melongena-virgin olive oil composition 2 times each week. He has has no side effects.

EXAMPLE 3

A 52 year old male suffering from hemorrhoids applied the Solanum melongena-virgin olive oil composition to the affected area 2 times daily for 6 weeks. Relief from pain occurred within 10 days and all the symptoms from hemorrhoids completely disappeared in 6 weeks time. No side effects were observed.

EXAMPLE 4

A 21 year male who was suffering from hemorrhoids applied the Solanum melongena-virgin olive oil composition to the affected area twice daily for 2 months. During that period of time all his symptoms completely disappeared and no side effects were observed.

EXAMPLE 5

A 48 year old male suffering for 12 years from hemorrhoids applied the Solanum melongena-virgin olive oil composition to the affected area 2 times daily for 6 weeks. After 1 week, relief from pain occurred and the hemorrhoids completely disappeared in the a period of 4 weeks. Extra applications were applied for safety reasons for 2 more weeks. Over a period of 9 to 16 months hemorrhoids reappeared and in each case the Solanum melongena-virgin olive oil composition was applied. In each instance the hemorrhoids completely disappeared successfully without any side effects.

I claim:

1. A medicinal composition for the treatment of hemorrhoids and for skin care consisting essentially of an aqueous solution of genus *Solanum melongena* and virgin olive oil wherein the improvement comprises:

(a) cutting the outer skin from the stalk of a *Solanum melogena* plant;

(b) drying said outer skin from the stalk;

(c) grinding said skin into a fine powder;

(d) placing said powder into a receptacle containing boiling virgin olive oil and, (e) boiling the mixture of powder and virgin olive oil for approximately 30 minutes.

* * * * *